(12) United States Patent
Calisse

(10) Patent No.: US 7,914,571 B2
(45) Date of Patent: Mar. 29, 2011

(54) STENT WITH RADIOPAQUE MATERIAL

(75) Inventor: Jorge Calisse, Berlin (DE)

(73) Assignee: Abbott Laboratories Vascular Enterprises Limited, Dublin (IE)

(*) Notice: Subject to any disclaimer, the term of this patent is extended or adjusted under 35 U.S.C. 154(b) by 39 days.

(21) Appl. No.: 10/638,544

(22) Filed: Aug. 12, 2003

(65) Prior Publication Data

US 2004/0143320 A1 Jul. 22, 2004

(30) Foreign Application Priority Data

Aug. 13, 2002 (EP) .................................... 02018089

(51) Int. Cl.
*A61F 2/82* (2006.01)
(52) U.S. Cl. ....................................................... 623/1.34
(58) Field of Classification Search ................... 623/1.1, 623/1.15, 1.16, 23.64–26.7, 1.34, 1.44; 606/191–195
See application file for complete search history.

(56) References Cited

U.S. PATENT DOCUMENTS

| 4,922,905 | A  | * | 5/1990  | Strecker ........................ 606/195 |
| 5,607,422 | A  |   | 3/1997  | Smeets et al. |
| 5,725,572 | A  | * | 3/1998  | Lam et al. ..................... 623/1.16 |
| 6,174,330 | B1 | * | 1/2001  | Stinson ......................... 623/1.34 |
| 6,231,598 | B1 | * | 5/2001  | Berry et al. ................... 623/1.15 |
| 6,287,331 | B1 | * | 9/2001  | Heath ............................ 623/1.15 |
| 6,364,902 | B1 | * | 4/2002  | Dickenson et al. ........... 623/1.15 |
| 6,387,123 | B1 | * | 5/2002  | Jacobs et al. ................. 623/1.34 |
| 6,471,721 | B1 | * | 10/2002 | Dang ............................. 623/1.34 |
| 6,626,936 | B2 | * | 9/2003  | Stinson ......................... 623/1.15 |
| 6,890,350 | B1 | * | 5/2005  | Walak ........................... 623/1.15 |

FOREIGN PATENT DOCUMENTS

EP 1 016 422 A1 7/2000
WO WO 01/93781 A2 12/2001

* cited by examiner

*Primary Examiner* — Corrine M McDermott
*Assistant Examiner* — Megan Wolf
(74) *Attorney, Agent, or Firm* — Workman Nydegger

(57) ABSTRACT

A stent is configured having a tubular, flexible body. The body of the stent has a wall which is formed by a web structure. The stent further contains a portion with radiopaque material. This radiopaque material is integrated in the material of the body of the stent.

18 Claims, 2 Drawing Sheets

STENT WITH RADIOPAQUE MATERIAL

BACKGROUND OF THE INVENTION

1. Field of the Invention

This invention generally relates a stent. More specifically, the present invention relates to a stent comprising a tubular flexible body having a wall formed by a web structure and having a radiopaque portion.

2. Background Information

Very different types of stents are already known from the prior art. Stents form a vascular prosthesis made from a physically compatible material. The stent is used for expanding blood vessels or also other body orifices and for keeping the vessels in their expanded state. To this end, the stent is positioned in a patient's body in its non-expanded state and is then expanded by suitable means, i.e. a balloon catheter. During expansion the individual web portions of the stent are deformed such that the stent permanently remains in its expanded form.

For a better localization of the stent in the patient's body the stents are made of metal or stainless steel or the like. Nowadays the stents become thinner so that even the metallic stents can not be localized. Therefore, some stents are covered with a radiopaque coating. The U.S. Pat. No. 5,607,442 discloses a stent that is plated with a high densitiy radiopaque metal such as gold or tantalum. The teaching of this patent shows a stent which is plated to a sufficient thickness on its longitudinal wires to make it clearly radiopaque in fluroscopy. This has the advantage, that the stent can clearly be viewed. On the other hand, the metallic stent plated with a radiopaque metal has the disadvantage that, if the boundary surface between the two materials comes into contact with blood or another water-containing fluid the stent may be corrupted by electrolytic corrosion. Furthermore, the coating of the stent with materials like gold is relatively expensive.

Another possible solution is to attach a portion containing the radiopaque material to the web structure. In this case, there is an area where the two materials are in contact together. Normally, both materials are made of metal. If blood flowing through the vessel comes into contact with the two different metals, electrolytic corrosion will occur which will lead to a damage of the stent and/or to an irritation of the vessel.

With regard to the state of the art there is a strong demand for creating a stent with a thin surface and which is sufficiently radiopaque so that it can be visualized under fluroscopy without the disadvantage of electrolytic corrosion.

In view of the above, it will be apparent to those skilled in the art from this disclosure that there exists a need for an improved stent. This invention addresses this need in the art as well as other needs, which will become apparent to those skilled in the art from this disclosure.

SUMMARY OF THE INVENTION

One object of the present invention is to provide a stent with a thin surface and which is sufficiently radiopaque so that it can be visualized under fluroscopy without the disadvantage of electrolytic corrosion.

To achieve this object, the invention proposes a stent having the features a tubular, flexible body having a wall and having a radiopaque portion such that radiopaque material of the radiopaque portion is integrated in the material of the body. The advantage of such a stent is that the radiopaque material is totally included in the material of the stent body or in other words the radiopaque material is totally coated by the body. Nevertheless, the radiopaque material of the stent is visible under fluroscopy or X-ray. This leads to the effect that the stent is visible due to the radiopaque portions even if the flexible body of the stent is made of a very thin web structure.

The stent of the invention is characterized by several considerable advantages.

Preferably the radiopaque material is included in at least one portion and at least one foreside part of the body of the stent, for example, at an axial ends thereof. The body of the stent preferentially has holes for containing the radiopaque material. For example, the holes can be drilled with a laser. A stent according to this invention can include the holes in form of a blind hole. In this case, the radiopaque material is included in the blind hole.

The holes or blind holes containing the radiopaque material can be arranged in axial orientation. The hole is extending from the foreside part of the body of the stent.

The holes are closed on at least one side to prevent the radiopaque material from dropping out of the hole. There are several preferred methods of closing such a hole. Preferentially, the holes are closed by riveting, welding, sticking or the like, so that the radiopaque material is totally surrounded by the material of the body of the stent. The outer surface of the stent is only made of one material. There is no area where the two materials, the material of the body and the radiopaque material, can get into contact with blood flowing through the deployed stent. This has the advantage that an electrolytic corrosion of the stent is avoided.

These and other important objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure.

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
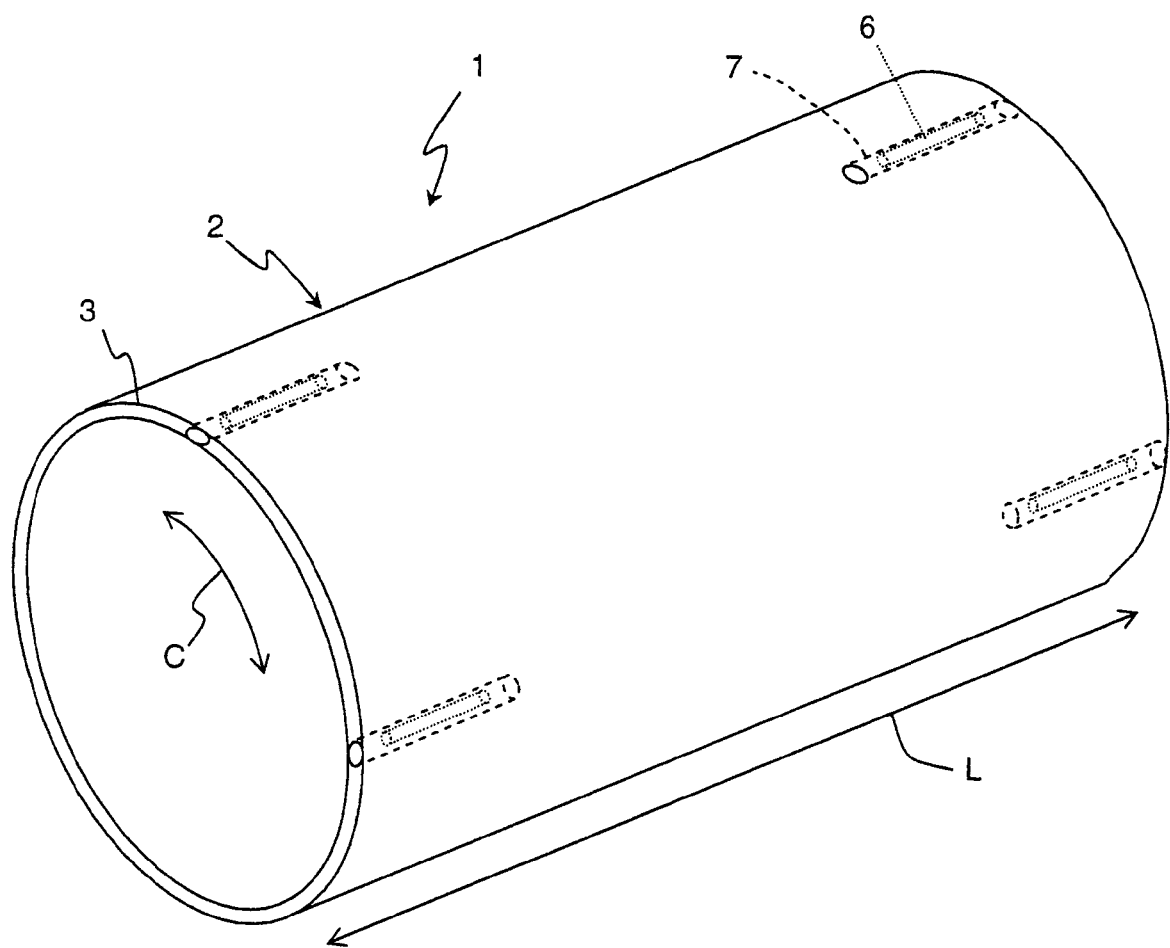
FIG. 1 is a schematically very simplified illustration of the basic structure of a stent according to the present invention.

Referring initially to FIG. 1, an inventive stent 1 is illustrated in accordance with a first embodiment of the present invention. FIG. 1 illustrates the fundamental structure of an inventive stent 1. The stent 1 basically comprises a flexible tubular body 2 with a tubular wall 3 with a longitudinal direction L and a circumferential direction C. The stent 1 according to the present invention can be designed as a balloon-expandable or self-expandable stent. The wall 3 of the body 2 of the stent 1 has a stent web structure 4 which can be transformed from a non-expanded state (compressed) into an expanded state. To this end the stent web structure 4 comprises a plurality of neighboring web patterns, of which only portions of web patterns are illustrated in FIG. 2a by way of example.

Figure 2A:
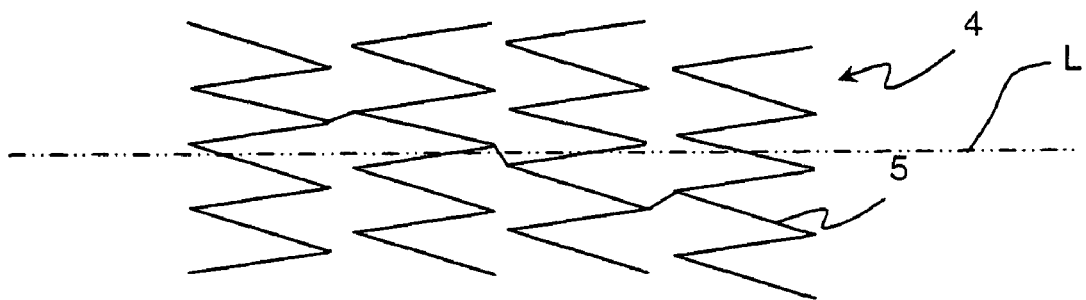
FIG. 2a is an illustration of the web structure of the wall of the stent.
Figure 2B:
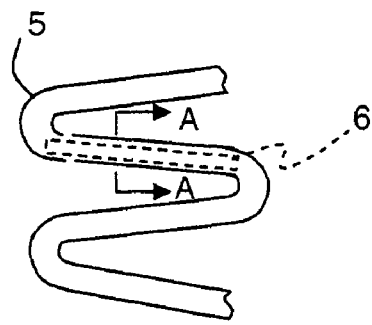
FIG. 2b is an enlarged illustration of the foreside part of the stent.

FIG. 2a shows the construction of the web structure 4 of the invention in detail. FIG. 2b shows a view through a magnifying glass to illustrate the web structure 4 of FIG. 2a in more detail. The single web 5 formed like a V or a S includes a segment of radiopaque material, i.e. radiopaque wire.

Figure 2C:
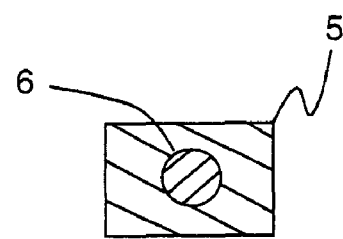
FIG. 2c is a cross-sectional view of the web structure of the stent as seen through section line A-A of FIG. 2b.

The cross section view in FIG. 2c between A-A shows that the radiopaque material 6 is totally surrounded by the material of the web 5. It is important that the diameters of the radiopaque material 6, which is formed like a tube, is adjusted to the diameter or minimum width of the web 5 which is also called strut. The diameter of the radiopaque material 6 always has to be smaller than the diameter or minimum width of the web 5. Typically dimensions are 0.05 mm diameter of the radiopaque material 6 positioned in a strut or web 5 with a minimum width of 0.09 mm. If the strut 5 has a minimum width of 0.22 mm, the radiopaque material 6 has a diameter of 0.15 mm. In a web 5 having a 0.16 mm thickness, the radiopaque material 6 with a diameter of 0.1 mm can be inserted.

Figures 3A, 3B:
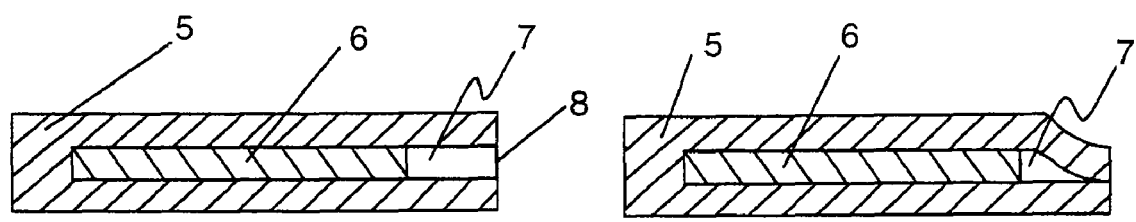
FIG. 3a is a detailed illustration of one web of the stent of the present invention before riveting.
FIG. 3b shows the web of the stent of the present invention shown in FIG. 3a after riveting.

FIG. 3a shows a part of the web in a longitudinal cut. A blind hole can be drilled into the web 5 with a laser beam or with an eroding machine. This blind hole 7, which is confined within a single strut or web 5 of the web structure 4 with associated web pattern, is formed like a tube and has one opening 8 at one side. The side with the opening is the fronthead side of the wall 3 of the stent 1. Before riveting the web 5 of the stent 1 the radiopaque material 6 can be inserted in the blind hole 7. This segment made of radiopaque material 6 can be formed as a cylinder or as a part of a wire or the like. The blind hole 7 in the web 5 is larger than the radiopaque material 6, so that the radiopaque material is totally inserted in the web structure.

FIG. 3b shows the web of FIG. 3a after riveting. The opening 8 of the blind hole 7 in the web structure 4 is now closed. The radiopaque material 6 is totally included in the web 5 and has no contact to the outside. Closing the opening 8 of the blind hole 7 can be done by riveting or by pushing the two ends of the blind hole 7 together. Alternatively, the opening 8 of the blind hole 7 can be closed by welding with a laser beam or by other processes.

It is important that the procedure of closing the opening 8 of the blind hole 7 leads to a completely closed web 5 so that no blood can come into contact with the radiopaque material 6 for avoiding electrolytic corrosion.

The radiopaque material can be selected out of the group of platinum, gold, niobium, tantalum, barium sulfate powder or a polymer containing one of the before-mentioned materials.

The stent can be made from a material out of the group of stainless steel, nitinol, polymers or any other suitable biocompatible materials.

Moreover, terms that are expressed as "means-plus function" in the claims should include any structure that can be utilized to carry out the function of that part of the present invention.

The terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies. This application claims priority to European Patent Application No. 02018089.9-1257 filed on Aug. 13, 2002. The entire disclosure of European Patent Application No. 02018089.9-1257 is hereby incorporated herein by reference.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A stent comprising:
a tubular, flexible body formed of a material defining a longitudinal direction and a circumferential direction, the flexible body having a wall defining a permanent web structure defined by a plurality of neighboring web patterns and comprising a plurality of struts and configured to transition between a compressed state and an expanded state, the flexible body including a plurality of blind holes formed in at least one of the plurality of neighboring web patterns, the blind holes extending for less than the length of a single, longitudinally extending strut of the web pattern and being confined within the single, longitudinally extending strut of the web pattern, at least one of the plurality of blind holes being arranged to be orientated to extend from a fronthead side of the body in the longitudinal direction and terminating within the single strut of the web pattern; and
a plurality of discrete radiopaque inserts being disposed within the plurality of blind holes,
the radiopaque inserts being sealed within the blind holes such that the radiopaque inserts are totally surrounded by the material of the body of the stent to prevent contact with the external environment.

2. The stent according to claim 1, wherein the plurality of blind holes are formed by a drilling or erosion process.

3. The stent according to claim 1, wherein the plurality of blind holes are sealed by riveting.

4. The stent according to claim 1, wherein the plurality of blind holes are sealed by welding.

5. The stent according to claim 1, wherein the wall consists of a material selected from a group consisting of stainless steel, nitinol, and biocompatible polymers.

6. The stent according to claim 1, wherein the web structure comprises a series of V or S shaped webs.

7. The stent according to claim 1, wherein the radiopaque inserts consist of a material selected from a group consisting of platinum, gold, niobium, tantalum, barium sulfate powder and a polymer containing one of the before-mentioned materials.

8. The stent according to claim 1, wherein the plurality of blind holes are sealed by compressing the open end of each hole.

9. The stent according to claim 1, wherein the cross-section of each radiopaque insert is more than 50% of the cross-section of the strut, in which the radiopaque insert is disposed.

10. A stent comprising:
a tubular, flexible body formed of a material configured to transition between a compressed state and an expanded state, the flexible body defining a longitudinal direction and a circumferential direction and having a wall defining a permanent web structure defined by a plurality of connected neighboring web patterns, each web pattern comprising a plurality of struts, with a plurality of bends connecting the plurality of struts, with proximal-most and distal-most web patterns including a plurality of blind holes, each blind hole extending from a proximal-most or distal-most side of the body in a longitudinal direction, for less than the length of a single strut of the web pattern, and being confined and terminating within the single strut of the web pattern; and a plurality of discrete radiopaque inserts being disposed within the plurality of blind holes, the radiopaque inserts being sealed within the blind holes such that the radiopaque inserts are totally surrounded by the material of the body of the stent to prevent contact with the external environment.

11. The stent according to claim 10, wherein the plurality of blind holes are formed by a laser drilling or erosion process.

12. The stent according to claim 10, wherein the plurality of blind holes are sealed by riveting, welding, or sticking.

13. The stent according to claim 10, wherein the radiopaque insert has a diameter smaller than a diameter of the blind hole.

14. The stent according to claim 10, wherein the radiopaque insert is smaller than the blind hole.

15. The stent according to claim 10, wherein the wall consists of a material selected from a group consisting of stainless steel, nitinol, and biocompatible polymers.

16. The stent according to claim 10, wherein the radiopaque inserts consist of a material selected from a group consisting of platinum, gold, niobium, tantalum, barium sulfate powder and a polymer containing one of the beforementioned materials.

17. The stent according to claim 10, wherein the plurality of blind holes are sealed by compressing the open end of each hole.

18. The stent according to claim 10, wherein the cross-section of each radiopaque insert is more than 50% of the cross-section of the strut, in which the radiopaque insert is disposed.

* * * * *